United States Patent [19]

Kenna

[11] Patent Number: 4,552,136
[45] Date of Patent: Nov. 12, 1985

[54] FEMORAL RASP

[75] Inventor: Robert V. Kenna, Saddle River, N.J.

[73] Assignee: Howmedica, Inc., New York, N.Y.

[21] Appl. No.: 543,203

[22] Filed: Oct. 19, 1983

[51] Int. Cl.$^4$ .......................... A61F 5/04; A61F 17/32
[52] U.S. Cl. .................................. 128/92 E; 128/305; 128/92 R
[58] Field of Search ............... 128/92 E, 92 EB, 305, 128/312, 303 R, 92 R

[56] References Cited

U.S. PATENT DOCUMENTS

| | | | |
|---|---|---|---|
| 3,815,599 | 6/1974 | Deyerle | 128/92 E |
| 4,124,026 | 11/1978 | Berner et al. | 128/92 E |
| 4,306,550 | 12/1981 | Forte | 128/92 E |
| 4,466,429 | 8/1984 | Loscher et al. | 128/92 E |
| 4,473,070 | 9/1984 | Matthews et al. | 128/92 E |

OTHER PUBLICATIONS

Machinery's Handbook, P. B. Schubert (editor), 20th ed., 1978, "Broaches & Broaching", pp. 1932-1939.

Primary Examiner—John J. Wilson
Assistant Examiner—C. W. Shedd
Attorney, Agent, or Firm—Charles J. Knuth; Peter C. Richardson; Harold W. Ordway

[57] ABSTRACT

A femoral rasp for preparing an intramedullary canal for receiving the stem of a femoral hip prosthesis comprises a body section generally divided into a wide proximal portion and a substantially longer narrow distal portion. The body section has a shape that generally corresponds to the stem of a femoral hip prosthesis to be inserted into the prepared cavity. A plurality of spaced apart cutting teeth are located on selected portions of the outside surface of the body section for removing cancellous tissue and bone. A smooth surface on the lateral face of the body section at the free end of the distal portion prevents violation of the lateral cortex upon insertion of the body section into the intramedullary canal. Removal of the body section and insertion of the hip prosthesis results in a glove fit between the stem of the prosthesis and the cavity formed by the femoral rasp.

16 Claims, 9 Drawing Figures

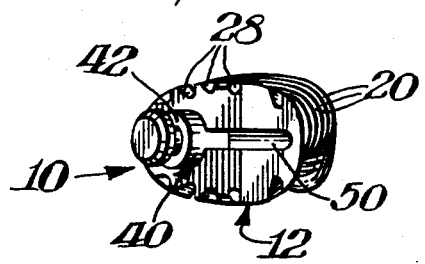
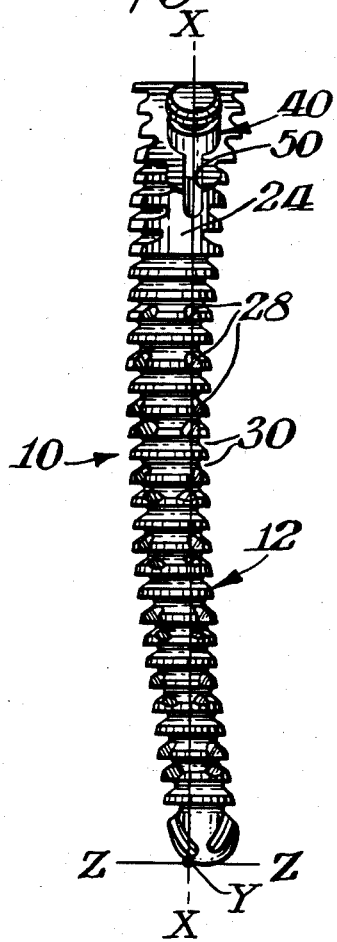
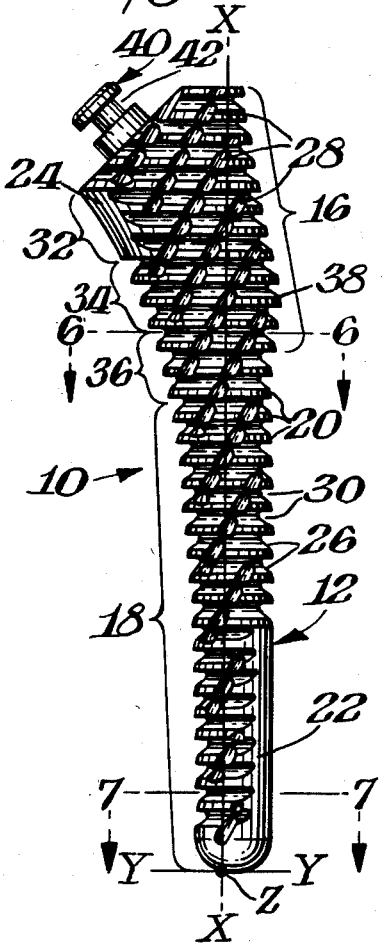
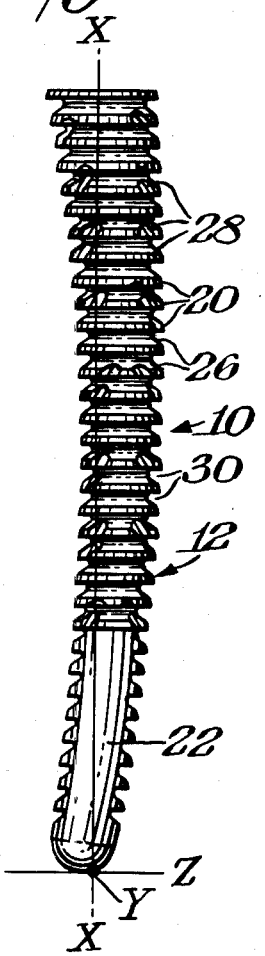
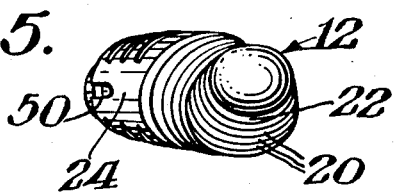

FEMORAL RASP

CROSS-REFERENCE TO RELATED APPLICATIONS

The present invention is related to the subject matter of applicant's copending applications Ser. No. 501,215, filed June 6, 1983, entitled Femoral Hip Prosthesis, and Ser. No. 485,368, filed Apr. 15, 1983, entitled Rasp Handle, the disclosures of which are incorporated herein by reference.

BACKGROUND OF THE INVENTION

The present invention relates to a femoral rasp for preparing an intramedullary canal for receiving the stem of a femoral hip prosthesis.

Hip arthroplasty procedure includes anesthesia and patient placement on a table in proper orientation. The patient's body is then stabilized, scrubbed, prepared and draped. Appropriate soft tissue is excised and/or divided for exposure and dislocation of the hip. After the femoral head is dislocated from its associated acetabulum, the head is rotated for better exposure. A femoral neck osteotomy is then performed wherein the head and neck are cut away from the femur shaft. Next, the intramedullary canal is prepared to accommodate the hip stem component of the prosthesis and, ultimately, the stem is anchored within the intramedullary canal.

Preparation of the intramedullary canal is an important step in the overall procedure since the fit between the stem and its associated femur is determined by the size of the prepared cavity. An improper fit of the stem within the cavity often causes rotation of the stem relative to the femur and improper articulation of the hip joint prosthesis.

Hence, the characteristics of the spacing or interface between the exterior surface of the femoral stem and the interior contour of the prepared cavity in the intramedullary canal play an important role in properly anchoring the femoral prosthesis to the femur. A stem of sufficient length has long been recognized as desirable since it provides increased resistance to rotation. However, long stems require large intramedullary cavities, particularly at the calcar leading into the canal, since the overall surface thereof makes it impossible for the insert to pass into the cavity without a significantly oversized entranceway. Such cavities formed by prior art implements produce large gaps or voids between the outside surface of the inserted stem and the inside surface of the cavity. Heretofore, a glove fit between a femoral stem and the intramedullary cavity together with superior anchoring of the stem and resistance to rotation have been considered difficult to achieve.

SUMMARY OF THE INVENTION

Accordingly, an object of the present invention is a femoral rasp used to form an intramedullary cavity that produces a glove fit between the femoral stem of the prosthesis and the cavity when the stem is inserted into the cavity.

In accordance with the present invention, a femoral rasp for preparing an intramedullary canal for receiving the stem of a femoral hip prosthesis comprises a body section generally divided into a wide proximal portion and a substantially longer narrow distal portion. The body section has a shape that generally corresponds to the stem of the femoral hip prosthesis to be inserted into the prepared intramedullary canal. A plurality of spaced apart cutting teeth on selected portions of the outside surface of the body section function to remove cancellous tissue and bone. A smooth surface on the lateral face of the body section at the free end of the distal portion prevents violation of the lateral cortex upon insertion of the body section into the intramedullary canal.

The body section has a long axis, and each of the cutting teeth is preferably arranged substantially normal to such long axis. Moreover, the majority of the cutting teeth extend completely around the body section. Each of the cutting teeth may have a cutting angle of about 78° and a relief angle of about 12°.

The femoral rasp herein also includes spaced apart channels in the anterior and posterior faces of the body section, the channels being diagonally arranged relative to the long axis of the body section and extending through the cutting teeth for receiving tissue and bone chips when the rasp is urged into the intramedullary canal. Such spaced apart diagonally arranged channels may extend about 60° to the long axis of the body section.

A smooth surface may also be located on the medial face of the body section at the free end of the proximal portion for protecting the medial cortex when the rasp is fully inserted into the intramedullary canal.

Preferably, the body section has a slight posterior bow along its length and a twist of from about 5° to 15° in the proximal portion, the twist extending in a direction from the anterior to the posterior face through the medial face. The length of the distal portion preferably is from about two or three times the length of the proximal portion as measured along the medial face. Also, it is preferred that the twist generally commence at the boundary of the distal and proximal portions, and that such twist extend through the proximal portion. The proximal portion may be generally equally divided into a proximal segment, a central segment and a distal segment with a lateral flare on the distal segment.

Preferably, the femoral rasp includes a shank section extending from the free end of the proximal portion of the body section, the shank having an axis at an angle of about 45° to the general orientation of the body section. When the rasp is fully positioned within the intramedullary canal, a trial capitulum is releasably connected to the shank to assist in determining the proper size of the capitulum for the femoral hip prosthesis to be inserted.

BRIEF DESCRIPTION OF THE DRAWING

Novel features and advantages of the present invention in addition to those mentioned above will become apparent to those skilled in the art from a reading of the following detailed description in conjunction with the accompanying drawing wherein:

FIG. 1 is a front elevational or anterior view of a left femoral rasp, according to the present invention;

FIG. 2 is a top plan view of the femoral rasp shown in FIG. 1;

FIG. 3 is a right side elevational or lateral view of the femoral rasp shown in FIG. 1;

FIG. 4 is a left side elevational or medial view of the femoral rasp shown in FIG. 1;

FIG. 5 is a bottom plan view of the femoral rasp shown in FIG. 1;

DETAILED DESCRIPTION OF THE INVENTION

Figure 6:
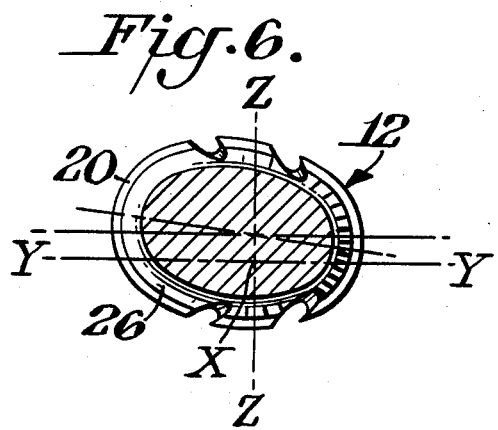
FIG. 6 is a sectional view taken along line 6—6 of FIG. 1.

Referring in more particularity to the drawing, a femoral rasp 10 comprises a body section 12 having an anterior face (FIG. 1), a lateral face (FIG. 3), a medial face (FIG. 4) and a posterior face (not shown) similar to the anterior face. As explained more fully below, femoral rasp 10 is used to prepare an intramedullary canal 14 for receiving the stem of a femoral hip prosthesis of the type illustrated and described in applicant's copending application Ser. No. 501,215, filed June 6, 1983, entitled Femoral Hip Prosthesis. Moreover, the femoral rasp 10 illustrated herein is used to prepare a cavity 15 in the left femur, it being understood that the invention is equally applicable to a femoral rasp for the right femur. In this regard, the femoral rasp for preparing the intramedullary canal of a right femur is simply a mirror image duplicate of the illustrated femoral rasp 10.

Body section 12 is generally divided into a wide proximal portion 16 and a substantially longer narrow distal portion 18. The length of distal portion 18 is preferably from about two to three times the length of proximal portion 16 as measured along the medial face (FIG. 1). Also, body section 12 has a shape that generally corresponds to the stem of the femoral hip prosthesis to be inserted into the prepared intramedullary cavity 15. This relationship between femoral rasp 10 and the stem of the prosthesis produces a glove fit between the stem and the prepared cavity 15 when the prosthesis is ultimately fitted to the anatomical femur.

A plurality of spaced apart cutting teeth 20 are located in the outside surface of body section 12 for removing cancellous tissue and bone when femoral rasp 10 is urged into the intramedullary canal 14. As shown in FIGS. 1, 3 and 4, body section 12 has a long axis X, and each of the cutting teeth 20 is arranged substantially normal to that axis. With the exception of the teeth at the free ends of distal portion 18 and proximal portion 16 of body section 12, the cutting teeth 20 extend across each of the four faces of body section 12. The lower teeth on distal portion 18 are interrupted by a smooth lateral surface 22, while the upper teeth on proximal portion 16 are interrupted by a smooth medial surface 24. As explained more fully below, lateral surface 22 prevents violation, or removal, of the lateral cortex upon insertion of body section 12 into intramedullary canal 14; in similar fashion, medial surface 24 protects the medial cortex when femoral rasp 10 is fully inserted.

Figure 8:
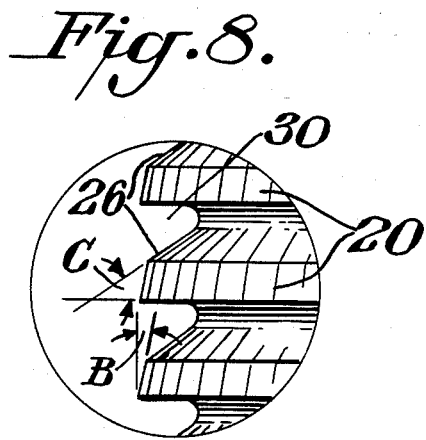
FIG. 8 is an enlarged detail of the cutting teeth.

FIG. 8 illustrates the details of cutting teeth 20 and shows that each tooth has a clearance angle B, which may be about 12°, and the trailing surface 26 behind each of the cutting teeth 20 has an incline C of about 25°.

As shown best in FIGS. 1 and 3, the anterior face of body section 12 includes spaced apart channels 28 diagonally arranged relative to the long axis X of body section 12. Channels 28 extend through the cutting teeth 20 for receiving tissue and bone chips when femoral rasp 10 is urged into intramedullary canal 14. Undercut spaces 30 between cutting teeth 20 and diagonal channels 28 function as repositories for the matter cut away from the femur during the formation of cavity 15 in intramedullary canal 14. Each of the diagonally arranged channels 28 extends about 60° to the long axis X of body section 12. The posterior face of body section 12 also includes a plurality of similarly arranged, spaced apart channels 28 partially illustrated in FIG. 3. Although the posterior channels are not fully illustrated, their orientation is a mirror image duplicate of the anterior channels.

Body section 12 has a slight posterior bow along its length. The posterior bow may be a curve having a radius of about 16 inches, for example, and follows the contour of the prosthesis stem to be inserted into prepared cavity 15. Also, proximal portion 16 of body section 12 includes a slight twist which generally commences at the boundary between distal portion 18 and proximal portion 16 and continues in an upward direction to the upper boundary of proximal portion 16. This total twist of generally from about 5° to 15°, preferably from about 7° to 12° and especially about 9°, in proximal portion 16 extends in a direction from the anterior face to the posterior face of body section 12 through the medial face thereof.

Figure 7:
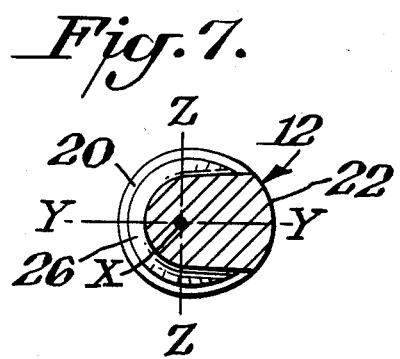
FIG. 7 is a sectional view taken along line 7—7 of FIG. 1.

This is best shown in the sectional views of FIGS. 6 and 7. FIG. 1 together with FIG. 6 show that horizontal axes Y and Z cross each other at 90°, and that the point of intersection forms the vertical or long axis X. Utilizing these coordinates, it is readily apparent from FIG. 7 that distal portion 18 is without twist. However, FIG. 6 clearly shows that the twist has commenced in the proximal portion 16, it being understood that such twist continues throughout the entire proximal portion 16 by an angular amount of about 9°, the especially preferred total twist.

Proximal portion 16 of body section 12 may be generally equally divided into a proximal segment 32, a central segment 34 and a distal segment 36. Distal segment 36 includes a flare 38 on the lateral side thereof. This geometry provides a complementary flare in the lateral surface of the prepared cavity 15 for receiving a similarly contoured flare on the stem of the prosthesis.

Femoral rasp 10 also includes a shank section 40 extending from the free end of proximal portion 16, shank section 40 having an axis at an angle of about 45° to the long axis X of body section 12. Shank section 40 has an annular depression 42 which cooperates with a suitable rasp manipulating device such as the rasp handle illustrated and described in applicant's copending application Ser. No. 485,368, filed Apr. 15, 1983, entitled Rasp Handle. The handle (not shown) is releasably attached to shank section 40 for driving body section 12 into the intramedullary canal, and also for removal purposes. Additionally, shank section 40 functions to releasably connect a trial capitulum 44 to femoral rasp 10. A socket 46 in trial capitulum 44 loosely fits over shank section 40 to provide the connection. As explained more fully below, the trial capitulum 44 is connected to femoral rasp 10 for fitting purposes and may include a tab or key 48 which fits in an appropriate recess 50 in femoral rasp 10 so that trial capitulum 44 is properly positioned relative to femoral rasp 10. The orientation of socket 46 and the location of key 48 are selected so that the trial capitulum 44 has the desired degree of anteversion when connected to shank section 40.

Figure 9:
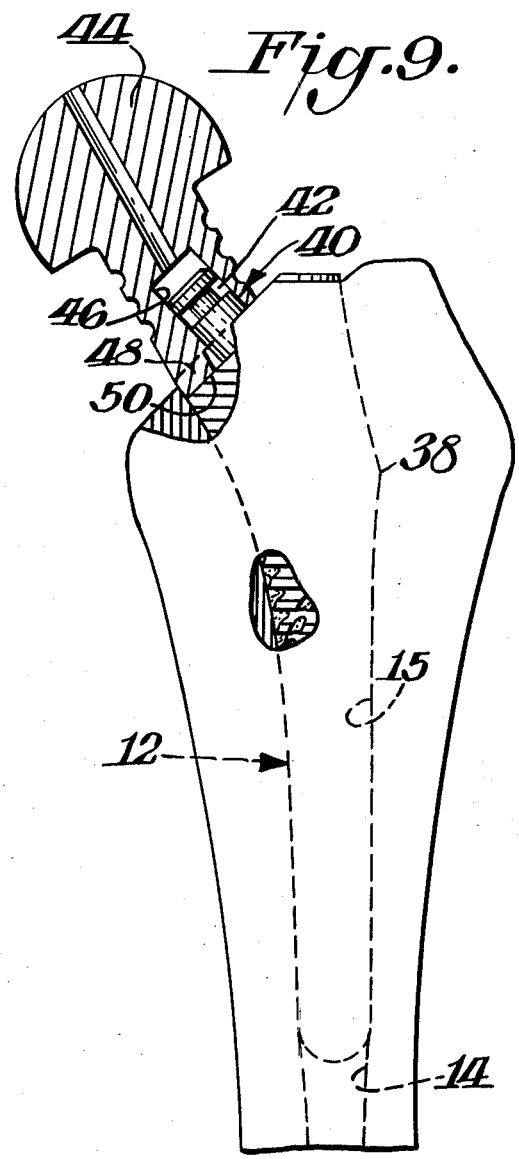
FIG. 9 is a view similar to FIG. 1 illustrating the femoral rasp positioned within the intramedullary canal of a femur with a trial capitulum releasably connected thereto.

Femoral rasp 10 is used in the following manner to prepare the intramedullary canal 14 for the stem of a femoral hip prosthesis having a shape that corresponds to body section 12. Following neck osteotomy, the portion of the cancellous tissue and calcar bone near the end of the anatomical femur is cut away with an appropriate cutting tool (not shown). Following such removal, femoral rasp 10 is driven into the intramedullary canal 14 until body section 12 is positioned as shown in FIG. 9. During the passage of the rasp into the canal, cutting teeth 20 remove cancellous tissue and bone, and such tissue and bone chips enter into the undercut spaces 30 between the teeth and into the diagonal channels 28. When body section 12 is initially introduced into intramedullary canal 14, smooth lateral surface 22 prevents violation, or removal, of the lateral cortex. Without the smooth lateral surface, the cutting teeth would gouge the lateral cortex and remove unwanted material, thereby causing a significant gap between prepared cavity 15 and the femoral stem. Similarly, smooth medial surface 24 protects the medial cortex when femoral rasp 10 is fully inserted into intramedullary canal 14. Such would not be the case if cutting teeth 20 extended into medial surface 24.

The handle or implement used to manipulate and drive femoral rasp 10 into intramedullary canal 14 is then removed from shank section 40 and a suitable trial capitulum 44 may be releasably connected to the shank to assist in properly fitting the prosthesis. Following the fitting procedure, trial capitulum 44 is removed and the rasp handle is again attached to shank section 40. Femoral rasp 10 is withdrawn from the prepared cavity 15 and any tissue or bone fragments remaining in the cavity are removed. The stem of the femoral prosthesis is then introduced into the thus formed cavity 15 without violating or interrupting the newly formed contour shaped by femoral rasp 10. The fit between the stem and cavity 15 is glovelike and substantially free of gaps or voids between the exterior surface of the stem and the interior contour of the cavity 15.

I claim:

1. A femoral rasp for preparing an intramedullary canal for receiving the stem of a femoral hip prosthesis, the rasp comprising a body section with anterior, posterior, lateral and medial faces and generally divided into a wide proximal portion and a substantially longer narrow distal portion, the body section having a shape that general corresponds to the stem of the femoral hip prosthesis to be inserted into the prepared intramedullary canal; a plurality of spaced apart cutting teeth on selected portions of the outside surface of the body section for removing cancellous tissue and bone, the majority of the cutting teeth extending across each of the four faces of the body section; and a smooth surface on the lateral face of the body section at the free end of the distal portion for preventing violation of the lateral cortex upon insertion of the body section into the intramedullary canal.

2. A femoral rasp as in claim 1 wherein the body section has a long axis, and each of the cutting teeth is arranged substantially normal to the long axis.

3. A femoral rasp as in claim 2 wherein each of the cutting teeth has a clearance angle of about 12°.

4. A femoral rasp as in claim 2 including spaced apart channels in the anterior and posterior faces diagonally arranged relative to the long axis of the body section and extending through the cutting teeth for receiving tissue and bone chips when the rasp is urged into the intramedullary canal.

5. A femoral rasp as in claim 4 wherein the spaced apart diagonally arranged channels extend about 60° to the long axis of the body section.

6. A femoral rasp as in claim 1 including a smooth surface on the medial face of the body section at the free end of the proximal portion for protecting the medial cortex when the rasp is fully inserted into the intramedullary canal.

7. A femoral rasp as in claim 1 including a shank section extending from the free end of the proximal portion, the shank section having an axis at an angle of about 45° to the general orientation of the body section.

8. A femoral rasp as in claim 7 in combination with a trial capitulum releasably connected to the shank section.

9. A femoral rasp for preparing an intramedullary canal for receiving the stem of a femoral hip prosthesis, the rasp comprising a body section with anterior, posterior, lateral and medial faces and generally divided into a wide proximal portion and a substantially longer narrow distal portion, the body section having a shape that generally corresponds to the stem of the femoral hip prosthesis to be inserted into the prepared intramedullary canal with a slight posterior bow along its length and a twist of from about 5° to 15° in the proximal portion, the twist extending in a direction from the anterior to the posterior face through the medial face; a plurality of spaced apart cutting teeth on selected portions of the outside surface of the body section for removing cancellous tissue and bone; and a smooth surface on the lateral face of the body section at the free end of the distal portion for preventing violation of the lateral cortex upon insertion of the body section into the intramedullary canal.

10. A femoral rasp as in claim 9 wherein the length of the distal portion is from about two to three times the length of the proximal portion as measured along the medial face.

11. A femoral rasp as in claim 9 wherein the twist generally commences at the boundary of the distal and proximal portions.

12. A femoral rasp as in claim 11 wherein the twist extends throughout the proximal portion.

13. A femoral rasp as in claim 12 wherein the twist is about 9°.

14. A femoral rasp as in claim 11 wherein the proximal portion is generally equally divided into a proximal segment, a central segment and a distal segment with a lateral flare on the distal segment.

15. A femoral rasp as in claim 14 wherein the body section has a long axis and each of the cutting teeth is arranged substantially normal to the long axis.

16. A femoral rasp as in claim 15 including spaced apart channels in the anterior and posterior faces diagonally arranged relative to the long axis of the body section and extending through the cutting teeth for receiving tissue and bone chips when the rasp is urged into the intramedullary canal.

* * * * *